US00PP32259P3

(12) United States Plant Patent
Nontaswatsri

(10) Patent No.: US PP32,259 P3
(45) Date of Patent: Sep. 29, 2020

(54) ***CURCUMA* PLANT NAMED 'PINK MAGIC'**

(50) Latin Name: ***Curcuma* hybrid**
Varietal Denomination: Pink Magic

(71) Applicant: Agricultural Research Development Agency, Bangkok (TH)

(72) Inventor: Chalermsri Nontaswatsri, Bangkok (TH)

(73) Assignee: Agricultural Research Development Agency, Bangkok (TH)

( * ) Notice: Subject to any disclaimer, the term of this patent is extended or adjusted under 35 U.S.C. 154(b) by 0 days.

(21) Appl. No.: 16/501,646

(22) Filed: May 16, 2019

(65) Prior Publication Data

US 2019/0357409 P1 Nov. 21, 2019

Related U.S. Application Data

(60) Provisional application No. 62/762,730, filed on May 17, 2018.

(51) Int. Cl.
*A01H 5/02* (2018.01)
*A01H 6/00* (2018.01)

(52) U.S. Cl.
USPC ..... Plt./421
CPC ..... *A01H 6/00* (2018.05); *A01H 5/02* (2013.01)

(58) Field of Classification Search
USPC ..... Plt./263.1, 421
See application file for complete search history.

*Primary Examiner* — Susan McCormick Ewoldt
*Assistant Examiner* — Karen M Redden
(74) *Attorney, Agent, or Firm* — The Webb Law Firm

(57) ABSTRACT

A new and distinct *Curcuma* plant having multi-colored inflorescences with a dominant pink color.

1 Drawing Sheet

Botanical classification: *Curcuma* hybrid.
Varietal denomination: 'Pink Magic'.

BACKGROUND OF THE INVENTION

The present invention comprises a new and distinct variety of *Curcuma* plant known by the varietal name 'Pink Magic'. The new variety was discovered in 2016 in Chiangmai, Thailand as the result of a planned breeding program with the purposes of providing *Curcuma* plants with new coloration and characteristics. The new variety is the result of a cross between an unnamed and unpatented *Curcuma alismatifolia* variety (female parent) and an unnamed and unpatented *Curcuma aurantiaca* variety (male parent). The new variety is similar to its female parent in exhibiting large upper inflorescence bracts, but differs from its female parent in lower inflorescence bract color (reddish brown for 'Pink Magic' compared to green for its female parent). 'Pink Magic' exhibits a similar lower inflorescence bract color to its male parent, but exhibits larger upper inflorescence bracts than its male parent. Tissue culture and bulb asexual reproductions of the new variety first occurred in 2016 in Chiangmai, Thailand. 'Pink Magic' has been trial and field tested and has been found to retain its distinctive characteristics and remain true to type through successive propagations. The present invention has not been evaluated under all possible environmental conditions. The phenotype may vary with variations in environment without a change in the genotype of the plant.

Its large upper inflorescence bract size and overall inflorescence coloration distinguish 'Pink Magic' from other *Curcuma* varieties known to the breeder. Further, when 'Pink Magic' is compared to *Curcuma* hybrid 'Pink Neon'

(U.S. Plant patent application Ser. No. 16/501,645), the varieties are similar in exhibiting multi-colored inflorescences with a dominant pink color. However, the leaves of 'Pink Neon' are narrower than those of 'Pink Magic' and 'Pink Neon' exhibits upper flower bracts that are elliptic in shape, while the upper flower bracts of 'Pink Magic' are oblong in shape.

DESCRIPTION OF THE DRAWING

The accompanying photographic drawing taken at approximately 60 days of age illustrates the new variety, with the colors being as nearly true as is possible with color illustrations of this type.

DESCRIPTION OF THE PLANT

The following detailed description sets forth the characteristics of the new variety at approximately 60 days of age. The data which defines these characteristics was collected under natural light in Chiangmai, Thailand. Plants of the new variety were grown in 20.3 cm pots in a plastic greenhouse in Chiangmai, Thailand and watered 1-2 times a day, if needed. Color references are primarily to the 2016 HTML Colour Chart and The 2015 R.H.S. Colour Chart of The Royal Horticultural Society of London, 6th Edition, except where general color terms are used.

PLANT

Time to initiate roots: About 20-30 days at about 30-33° C.
Time to produce a rooted young plant: About 45 days at about 30-33° C.
Root description: Fibrous, with a pale brown colored (A57C55) milk tank.
Number of rhizomes produced per plant: From 1-3.

Rhizome diameter: 4.0 cm.
Growth habit: Annual.
Plant height (soil level to top of inflorescences): 40.0 cm.
Plant diameter: 30.0 cm.
Pubescence: Light pubescence present on both surfaces of leaves, as well as upper and lower bract lower surfaces.
Disease resistance/susceptibility: None observed.
Pest resistance/susceptibility: None observed.
Temperature tolerance: 20-40° C. or tropical climate conditions.
Drought tolerance: Unknown.
Seed/fruit: None observed to date.
Leaves:
*Arrangement*.—Alternate.
*Average number per plant*.—5.
*Length*.—25.0 cm.
*Width*.—10.0 cm.
*Shape of leaf* (*generally*).—Moderately elliptic.
*Shape of apex*.—Attenuate.
*Shape of base*.—Obtuse.
*Margin description*.—Entire.
*Texture*.—Upper surface: Smooth. Lower surface: Pubescence present.
*Aspect*.—Upright.
*Color*.—Young leaves: Upper surface: Green (C5E96E). Lower surface: Green (7BA058). Mature leaves: Upper surface: Green (578441). Lower surface: Green (3B631D).
*Veins*.—Appearance: Pinnate and penninerved. Color: Upper surface: Green (55783C). Lower surface: Green (55783C).
*Leaf sheaths*.—Length: 21.0 cm. Width: 2.5 cm. Texture: Upper surface: Smooth. Lower surface: Smooth. Color: Upper surface: RHS 142A. Lower surface: RHS 176B. Venation: Pattern: Parallel. Color: RHS 140B.

INFLORESCENCE

Inflorescence arrangement: 1 inflorescence per shoot.
Inflorescence number per plant: From 1-3.
Inflorescence length: 20.0 cm.
Inflorescence diameter: 8.0 cm.
Fragrance: None.
Flower bracts:
*Total number per inflorescence*.—Approximately 20.
*Upper bracts*.—Number: Approximately 10. Length: 4.0 cm. Width: 3.0 cm. Shape: Oblong. Apex: Acuminate. Base: Ovate. Margin: Entire. Texture: Upper surface: Smooth. Lower surface: Downy. Color: Upper surface: Pink (DF2477). Lower surface: Pink (C12E74).
*Lower bracts*.—Number: Approximately 10. Length: 3.0 cm. Width: 3.0 cm. Shape: Ovate. Apex: Mucronate. Base: U-shaped. Margin: Entire. Texture: Upper surface: Smooth. Lower surface: Downy. Color: Upper surface: Green (2E3919) with a brown (361A12) distal end. Lower surface: Green (2E3919) with a brown (361A12) distal end.

Flowers:
*Number per inflorescence*.—Approximately 50.
*Continuity of flowering*.—1 month.
*Lastingness of an individual flower*.—1-2 days.
*Length*.—3.0 cm.
*Diameter*.—2.0 cm.
*Appearance*.—Orchidaceous form.
*Upper petals*.—Upper surface color: Pale yellow (C2997F). Lower surface color: Pale yellow (C2997F).
*Lower petals*.—Upper surface color: Pale yellow (C2997F) with a purple (934267) lip and yellow (A66E2E) labellum ridge. Lower surface color: Pale yellow (C2997F) with a purple (934267) lip and yellow (A66E2E) labellum ridge.
*Flower buds*.—Length: 4.0 cm. Diameter: 1.0 cm. Shape: Round. Texture: Smooth. Color: RHS 8D.
*Sepals*.—Number: 3. Calyx arrangement: In overlapping circles. Length: 2.0 cm. Width: 0.5 cm. Overall shape: Elliptic. Apex: Elliptic. Base: Connected in a cone shape. Texture: Smooth (both surfaces). Color: Upper surface: RHS 10D. Lower surface: RHS 10D.
Peduncles:
*Length*.—20.0 cm.
*Diameter*.—1.0 cm.
*Texture*.—Downy.
*Angle*.—Upright.
*Color*.—Green (827912).

REPRODUCTIVE ORGANS

Stamens:
*Number*.—1.
Filament:
*Length*.—2.0 cm.
*Diameter*.—1.0 mm.
*Color*.—Pale cream (C6AE98).
Anthers:
*Shape*.—2-lobed.
*Length*.—5.0 mm.
*Color*.—Cream (B88967).
Pollen: None observed.
Pistils:
*Number*.—1.
*Length*.—1.0 cm.
Style:
*Length*.—1.0 cm.
*Diameter*.—2.0 mm.
*Color*.—Pale cream (C6AE98).
Stigma:
*Length*.—2.0 mm.
*Diameter*.—2.0 mm.
*Color*.—Pale cream (C6AE98).

I claim:

1. A new and distinct variety of *Curcuma* plant, as is herein illustrated and described.

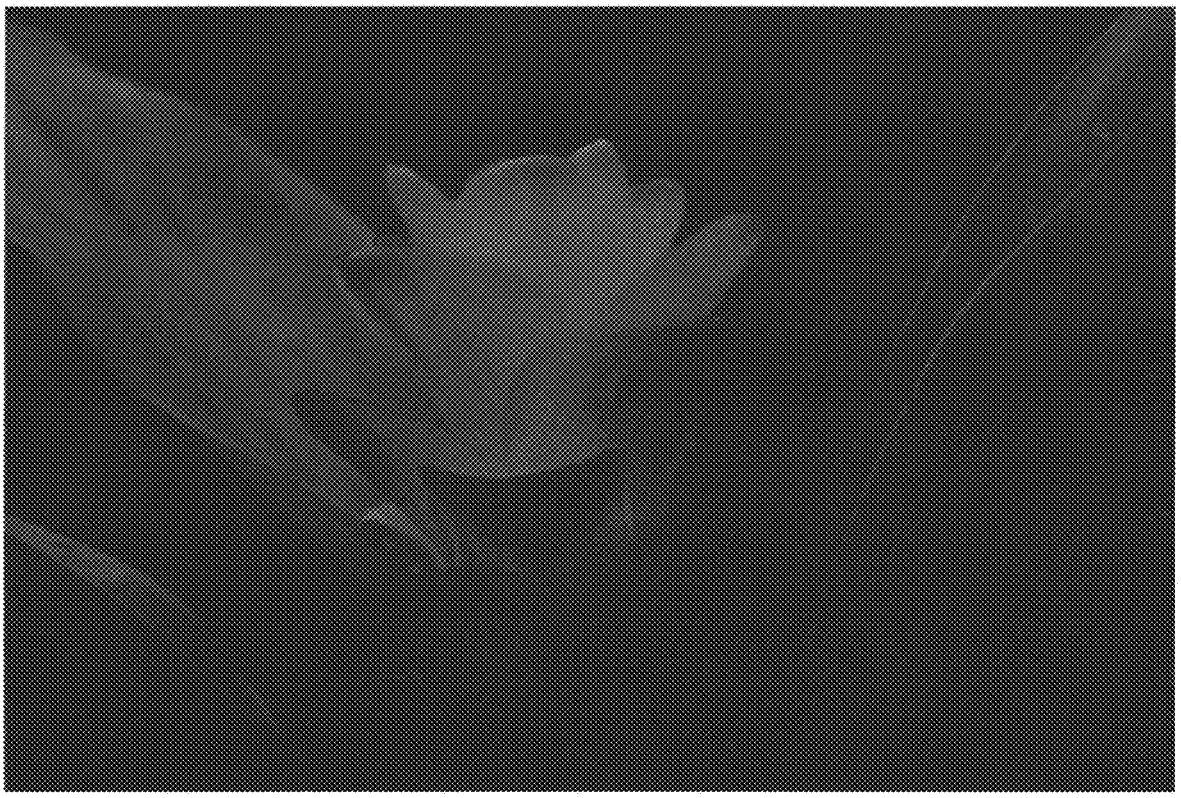

* * * * *